US009988242B1

(12) United States Patent
Lincoln et al.

(10) Patent No.: US 9,988,242 B1
(45) Date of Patent: Jun. 5, 2018

(54) ELEVATOR RAIL HEALTHY MONITORING METHOD

(71) Applicant: Otis Elevator Company, Farmington, CT (US)

(72) Inventors: David L. Lincoln, Johnston, RI (US); Michael J. Birnkrant, Wethersfield, CT (US); Wayde R. Schmidt, Pomfret Center, CT (US)

(73) Assignee: OTIS ELEVATOR COMPANY, Farmington, CT (US)

(*) Notice: Subject to any disclaimer, the term of this patent is extended or adjusted under 35 U.S.C. 154(b) by 0 days. days.

(21) Appl. No.: 15/403,771

(22) Filed: Jan. 11, 2017

(51) Int. Cl.
G01N 21/00 (2006.01)
B66B 7/12 (2006.01)
G01N 21/47 (2006.01)
G01N 21/952 (2006.01)
B66B 9/00 (2006.01)

(52) U.S. Cl.
CPC .......... *B66B 7/1207* (2013.01); *B66B 7/1238* (2013.01); *B66B 7/1246* (2013.01); *B66B 7/1253* (2013.01); *B66B 7/1276* (2013.01); *G01N 21/47* (2013.01); *G01N 21/952* (2013.01); *B66B 9/00* (2013.01); *G01N 2201/062* (2013.01); *G01N 2201/06113* (2013.01)

(58) Field of Classification Search
CPC ............... G01N 21/47; G01N 21/55; G01N 2021/4707; G01N 33/2888; B66B 7/1215
See application file for complete search history.

(56) References Cited

U.S. PATENT DOCUMENTS

| 4,667,231 | A | | 5/1987 | Pryor | |
|---|---|---|---|---|---|
| 5,331,169 | A | * | 7/1994 | Tanaka | G01N 21/88 250/358.1 |
| 5,760,888 | A | | 6/1998 | Rottenkolber | |
| 5,889,239 | A | | 3/1999 | Blackaby et al. | |
| 6,122,047 | A | * | 9/2000 | Stover | G01N 21/94 356/237.3 |
| 6,401,872 | B1 | | 6/2002 | Morishita | |
| 6,674,531 | B2 | | 1/2004 | Maehner | |
| 7,024,780 | B2 | | 4/2006 | Pfenniger | |

(Continued)

FOREIGN PATENT DOCUMENTS

CN 103615992 A 3/2014
DE 102015007054 A1 12/2016
(Continued)

OTHER PUBLICATIONS

ISR/WO dated Apr. 10, 2018 in U320807PCT, PCT Application No. PCT/US2018/013104, 12 pages.

Primary Examiner — Kara E Geisel
Assistant Examiner — Maurice Smith
(74) Attorney, Agent, or Firm — Cantor Colburn LLP

(57) ABSTRACT

A method of monitoring component health is provided. The method includes moving a health monitor over a scattering surface of the component, emitting light of various wavelengths toward the scattering surface from a light source of the health monitor, observing one or more responses of the scattering surface to the light of the various wavelengths at a detector of the health monitor and identifying a condition of the scattering surface from the observed one or more responses of the scattering surface to the light of the various wavelengths.

20 Claims, 6 Drawing Sheets

(56) References Cited

U.S. PATENT DOCUMENTS

| | | | |
|---|---|---|---|
| 7,588,127 B2 | 9/2009 | Shiratsuki et al. | |
| 8,045,179 B1 | 10/2011 | Zhuang et al. | |
| 9,399,562 B2 | 7/2016 | Terry et al. | |
| 2007/0062763 A1* | 3/2007 | Shiratsuki | B66B 1/3492 |
| | | | 187/394 |
| 2007/0163352 A1 | 7/2007 | Nielsen et al. | |
| 2007/0296975 A1* | 12/2007 | Butler | G01N 21/55 |
| | | | 356/429 |
| 2008/0056752 A1* | 3/2008 | Denton | G03G 15/5062 |
| | | | 399/74 |
| 2009/0319197 A1* | 12/2009 | Villar | B61K 9/08 |
| | | | 702/34 |
| 2010/0227943 A1* | 9/2010 | Coretsopoulos | C08F 2/48 |
| | | | 522/182 |
| 2011/0194864 A1* | 8/2011 | Nakatake | G03G 15/0877 |
| | | | 399/27 |
| 2012/0044968 A1* | 2/2012 | Haran | G01N 21/05 |
| | | | 374/17 |
| 2012/0134693 A1* | 5/2012 | Hoshi | G03G 15/5029 |
| | | | 399/45 |
| 2015/0217972 A1 | 8/2015 | Hawkins et al. | |
| 2016/0252490 A1 | 9/2016 | Shirata et al. | |

FOREIGN PATENT DOCUMENTS

| | | |
|---|---|---|
| JP | H03255937 A | 11/1991 |
| JP | H0434347 A | 2/1992 |
| WO | 2014039496 A2 | 3/2014 |

\* cited by examiner

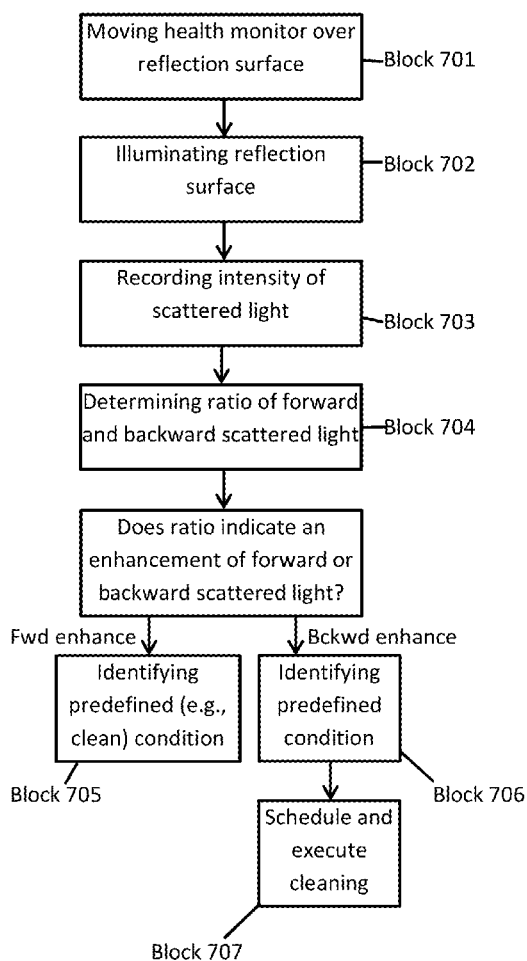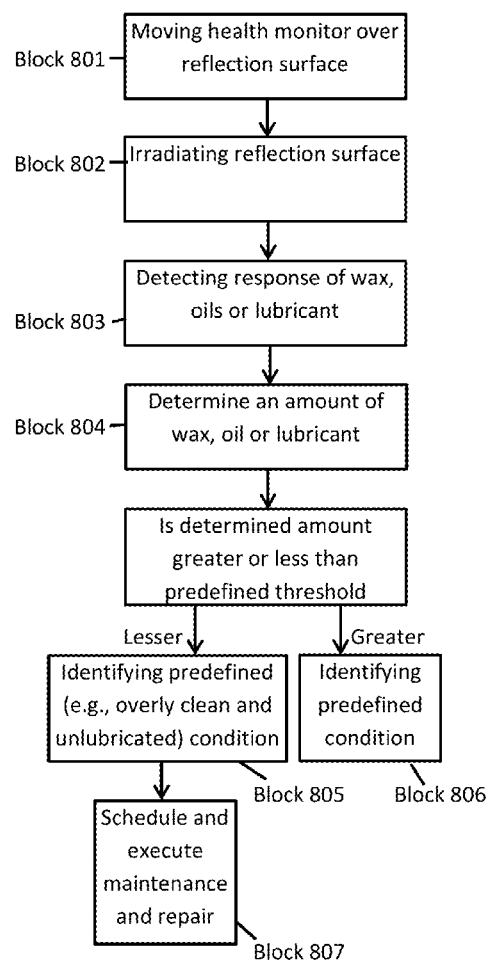

US 9,988,242 B1

ELEVATOR RAIL HEALTHY MONITORING METHOD

BACKGROUND

The following description relates to elevators and, more particularly, to methods of monitoring elevator rail health with a sensor.

A typical elevator system can include an elevator car that is configured to move vertically upward and downward within a hoistway along a plurality of guide rails as well as a counterweight. The counterweight is configured to move vertically upward and downward within the hoistway in a direction generally opposite the movement of the elevator car and is guided by counterweight guide rails. The elevator car also has doors that open and close to allow passengers to enter and exit at multiple floors.

Before the elevator system can be deployed and during its operational lifetime thereafter, inspection and maintenance is regularly conducted so that unsafe conditions can be addressed and mitigated. Often, the inspection and maintenance deal with conditions of the guide rails and the counterweight guide rails and require that an operator enter into the hoistway to conduct a visual inspection of guide rail surfaces. Repair and replacement of those guide rails that are deemed to be faulty for any reason is then conducted on the basis of the results of the visual inspection.

While such procedures are useful in evaluating guide rail health in many instances, the requirement that the operator enter into the hoistway to conduct the visual inspection is costly and time consuming. Moreover, the operator cannot easily compare a condition of a given guide rail at one time to the condition of that same guide rail at another time. Thus, the operator is generally incapable of making a determination as to guide rail conditional changes over time.

BRIEF DESCRIPTION

In accordance with an aspect of this disclosure, a method of monitoring component health is provided and includes moving a health monitor over a scattering surface of the component, emitting light of various wavelengths toward the scattering surface from a light source of the health monitor, observing one or more responses of the scattering surface to the light of the various wavelengths at a detector of the health monitor and identifying a condition of the scattering surface from the observed one or more responses of the scattering surface to the light of the various wavelengths.

In accordance with additional or alternative embodiments, the light source includes one or more light sources and the detector includes one or more photodetectors.

In accordance with additional or alternative embodiments, the emitting includes illuminating the scattering surface at an angle from the light source, the observing includes recording an intensity of scattered light scattered off the scattering surface at the detector and the identifying of the condition includes determining from the recorded intensity a ratio of forward scattered light to backward scattered light of the scattered light that is scattered off the scattering surface and identifying that the scattering surface exhibits one or more of an unclean, a rusted, a corroded, a chipped, a scratched, a dented, a burred, a cracked or a fractured condition in an event the determined ratio indicates an enhancement of the backward scattered light relative to the forward scattered light to a predefined degree.

In accordance with additional or alternative embodiments, the emitting includes irradiating the scattering surface with radiation from the light source at a wavelength selected for detecting wax, oil, debris or lubricant on the scattering surface, the observing includes detecting a response of the wax, oil, debris or lubricant on the scattering surface to the radiation at the detector and the identifying includes determining from the detected response an amount of the wax, oil, debris or lubricant on the scattering surface and identifying that the scattering surface exhibits an unclean and appropriately lubricated condition in an event the determined amount exceeds a predefined threshold.

In accordance with additional or alternative embodiments, the method is repeatable with respect to the scattering surface and includes measuring conditional changes of the scattering surface over time and scheduling and executing a cleaning, maintenance, repair or lubrication of the scattering surface in accordance with a result of the identifying.

In accordance with additional or alternative embodiments, the method further includes accounting for ambient light in the observing and identifying.

In accordance with another aspect of this disclosure, a method of monitoring elevator rail, rope or belt health is provided and includes moving a health monitor over a scattering surface, illuminating the scattering surface with light emitted from a light source of the health monitor, recording an intensity of scattered light scattered off the scattering surface and received by a detector of the health monitor, determining, from the recorded intensity of scattered light, a ratio of forward scattered light to backward scattered light of the scattered light that is received by the detector and identifying that the scattering surface exhibits a predefined condition in an event the determined ratio indicates an enhancement of the backward scattered light relative to the forward scattered light to a predefined degree.

In accordance with additional or alternative embodiments, the illuminating includes illuminating the scattering surface at an angle.

In accordance with additional or alternative embodiments, the light source includes one or more light sources.

In accordance with additional or alternative embodiments, the detector includes one or more photodetectors.

In accordance with additional or alternative embodiments, the identifying includes identifying that the scattering surface exhibits one or more of a clean, a non-rusted, a non-corroded, a non-chipped, a non-scratched, an undented, an un-burred, a non-cracked and a non-fractured condition in an event the determined ratio indicates an enhancement of the forward scattered light relative to the backward scattered light to a first predefined degree and identifying that the scattering surface exhibits one or more of an unclean, a rusted, a corroded, a chipped, a scratched, a dented, a burred, a cracked or a fractured condition in an event the determined ratio indicates an enhancement of the backward scattered light relative to the forward scattered light to a second predefined degree.

In accordance with additional or alternative embodiments, the method is repeatable with respect to the scattering surface and includes measuring conditional changes of the scattering surface over time.

In accordance with additional or alternative embodiments, the method further includes scheduling and executing a cleaning, maintenance or repair of the scattering surface in accordance with a result of the identifying.

In accordance with yet another aspect of this disclosure, a method of monitoring elevator rail, rope or belt health is provided and includes moving a health monitor over a scattering surface, irradiating the scattering surface with radiation emitted from an emitter of the health monitor at a wavelength selected for detecting wax, oil, debris or lubricant on the scattering surface, detecting a response of the wax, oil, debris or lubricant on the scattering surface to the radiation at a detector of the health monitor, determining from the detected response an amount of the wax, oil, debris or lubricant on the scattering surface and identifying that the scattering surface exhibits a predefined condition in an event the determined amount exceeds a predefined threshold.

In accordance with additional or alternative embodiments, the irradiating includes irradiating the scattering surface at an angle.

In accordance with additional or alternative embodiments, the light source includes an ultraviolet (UV) light emitting diode (LED), an organic light emitting diode (OLED) or a UV laser and the detector includes an ultraviolet (UV) sensitive photodetector.

In accordance with additional or alternative embodiments, the light source includes a light emitting diode (LED), an organic light emitting diode (OLED) or a laser that is tuned to visible or infrared (IR) wavelengths and the detector includes a complementary wavelength sensitive photodetector.

In accordance with additional or alternative embodiments, the identifying includes identifying that the scattering surface exhibits a clean an unlubricated condition in an event the determined amount is less than the predefined threshold and identifying that the scattering surface exhibits an unclean and appropriately lubricated condition in an event the determined amount exceeds the predefined threshold.

In accordance with additional or alternative embodiments, the method is repeatable with respect to the scattering surface and includes measuring conditional changes of the scattering surface over time.

In accordance with additional or alternative embodiments, the method further includes scheduling and executing a lubrication of the scattering surface in accordance with a result of the identifying.

BRIEF DESCRIPTION OF THE DRAWINGS

The subject matter, which is regarded as the disclosure, is particularly pointed out and distinctly claimed in the claims at the conclusion of the specification. The foregoing and other features, and advantages of the disclosure are apparent from the following detailed description taken in conjunction with the accompanying drawings in which:

FIG. 7 is a flow diagram illustrating a method of monitoring elevator rail health in accordance with embodiments; and FIG. 8 is a flow diagram illustrating a method of monitoring elevator rail health in accordance with embodiments.

DETAILED DESCRIPTION

As will be described below, methods of monitoring component health are provided. The components can be elevator components, such as scattering surfaces of guide rails, ropes or belts, or components of any system that moves in repeatable patterns. The methods include moving a health monitor over a scattering surface of the component, emitting light of various wavelengths toward the scattering surface from a light source of the health monitor, observing one or more responses of the scattering surface to the light of the various wavelengths at a detector of the health monitor and identifying a condition of the scattering surface from the observed one or more responses of the scattering surface to the light of the various wavelengths. The methods may further include a subtraction of ambient light from detected light by way of a first measurement by a light detector and a subsequent subtraction of that first measurement from a measurement of light scattered or fluoresced off a scattering surface. Alternatively, the subtraction could be implemented in hardware through a switching circuit that charges up a capacitor to a current equal to the ambient light and then switches to the measurement circuit and subtracts off the current equivalent to the ambient light.

Figure 1:
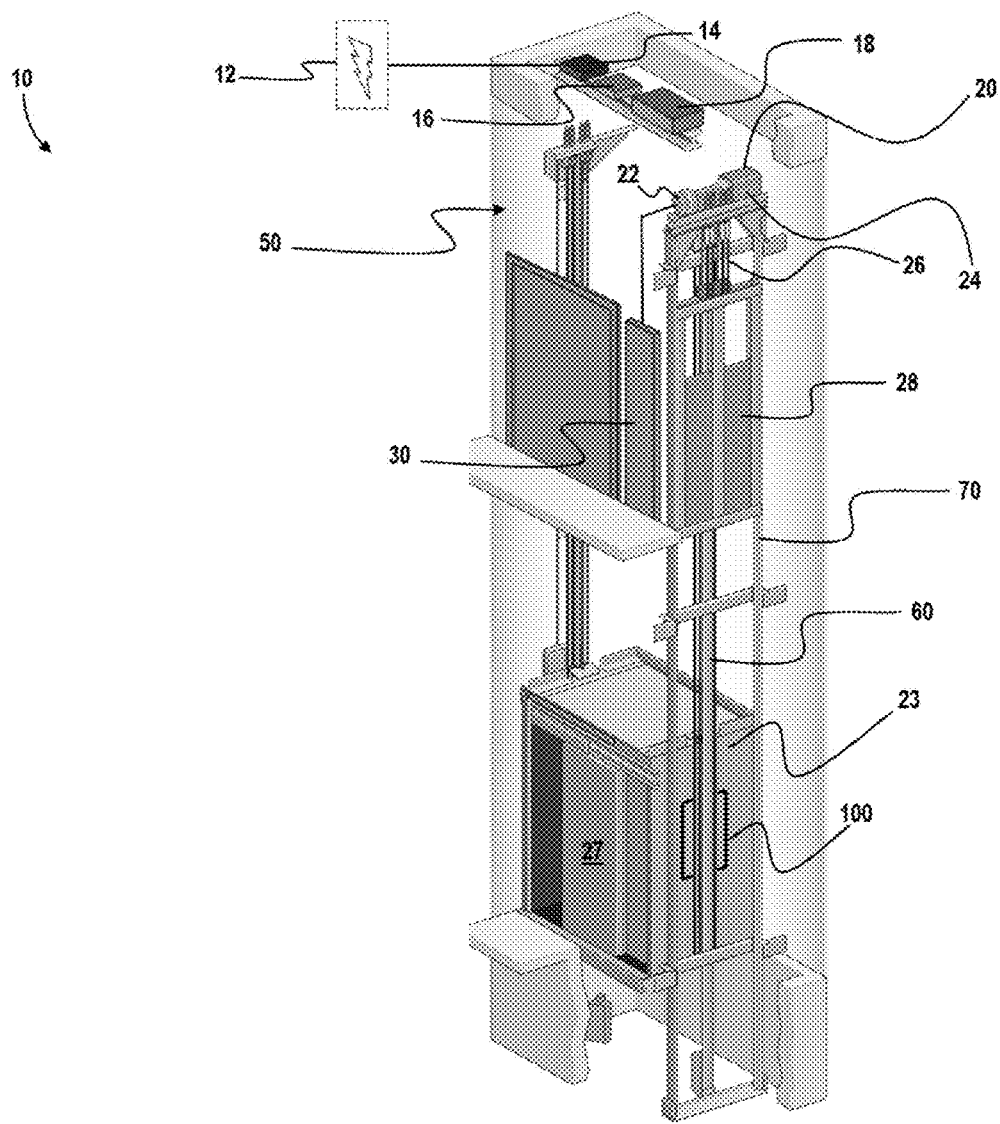
FIG. 1 illustrates a schematic view of an elevator system in accordance with embodiments.

With reference to FIG. 1, an elevator system 10 is provided. The elevator system 10 includes an elevator car 23 that is configured to move vertically upward and downward within a hoistway 50 along a plurality of guide rails 60. The elevator system 10 also includes a counterweight 28 that is operably connected to the elevator car 23 via a pulley system 26. The counterweight 28 is configured to move vertically upward and downward within the hoistway 50 in a direction generally opposite the movement of the elevator car 23. Movement of the counterweight 28 is guided by counterweight guide rails 70 mounted within the hoistway 50. The elevator car 23 has doors 27 that open and close to allow passengers to enter and exit.

The elevator system 10 also includes a power source 12. Power is provided from the power source 12 to a switch panel 14, which may include circuit breakers, meters, etc. From the switch panel 14, the power may be provided directly to drive unit 20 through a controller 30 or to an internal power source charger 16, which converts power in the form of alternating current (AC) to power in the form of direct current (DC) to thereby charge an internal power source 18 that requires charging. The internal power source 18 may be a battery, capacitor or any other type of power storage device. Alternatively, the internal power source 18 may not require charging from the power source 12 and may instead be a device such as a gas powered generator, solar cells, a hydroelectric generator, a wind turbine generator or a similar power generation device. In any case, the internal power source 18 may power various components of the elevator system 10 when an external power source is unavailable.

The drive unit 20 drives a machine 22 to impart motion to the elevator car 23 via a traction sheave of the machine 22. The machine 22 also includes a brake 24 that can be activated to stop the machine 22 and the elevator car 23.

As will be appreciated by those of skill in the art, FIG. 1 depicts a machine room-less elevator system 10. However, the embodiments disclosed herein may be incorporated with other elevator systems that are not machine room-less or that include any other known elevator configuration. In addition, elevator systems having more than one independently operating elevator car in each elevator shaft and/or rope-less elevator systems may also be used. In one embodiment, the elevator car may have two or more compartments.

The elevator system 10 also includes an elevator rail, rope or belt health monitoring system 100 which may be located on the elevator car 23 or on another similarly movable component of the elevator system 10 (e.g., the counterweight 28), or on multiple components. The elevator rail, rope or belt health monitoring system 100 will be discussed further below.

The controller 30 is responsible for controlling the operation of the elevator system 10. The controller 30 may also determine a mode (motoring, regenerative, near balance) of the elevator car 23 by use of the car direction and the weight distribution between the elevator car 23 and the counterweight 28. The controller 30 may also adjust a velocity of the elevator car 23 to reach a target floor. In any case, the controller 30 includes a processor and an associated memory. The processor may be, but is not limited to, a single-processor or multi-processor system of any of a wide array of possible architectures, including a field programmable gate array (FPGA) architecture, a central processing unit (CPU) architecture, application specific integrated circuit (ASIC) architectures, digital signal processor (DSP) or graphics processing unit (GPU) architectures and may include hardware arranged homogenously or heterogeneously. The processor may also be provided on-board a sensor itself for plug-and-play applications and for communication with the controller 30. The memory may be, but is not limited to, a random access memory (RAM), read only memory (ROM) or other electronic, optical, magnetic or any other computer readable medium.

Referring now to FIGS. 2-6C, the elevator rail, rope or belt health monitoring system 100 will be described in detail. The elevator rail or rope health monitoring system 100 is disposed in operative communication with the controller 30 and may be located on a side of the elevator car 23 opposite a scattering surface 60a. In the illustrated embodiment of FIG. 2, the elevator rail, rope or belt health monitoring system 100 is located on a side of the elevator car 23 opposite the guide rail 60 and thus the guide rail 60 acts as the scattering surface 60a. Alternatively, the elevator rail, rope or belt health monitoring system 100 may be located in various other locations having various other scattering surfaces 60a, such as, for example on the counterweight 28 opposite the counterweight guide rail 70 (the counterweight guide rail 70 being the scattering surface in this case), on the side of the elevator car 23 opposite a wall of the hoistway 50 (the wall of the hoistway 50 being the scattering surface in this case) and/or any surface that faces one or more of the ropes or belts of the pulley system 26 (the ropes or belts of the pulley system 26 being the scattering surface in such cases).

Figure 2:
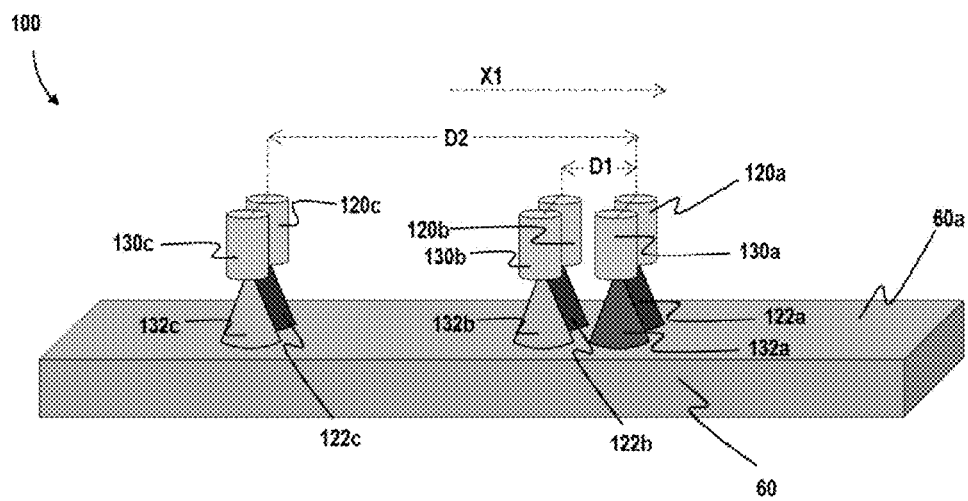
FIG. 2 illustrates a schematic view of an elevator rail health monitoring sensing system that may be incorporated into the elevator system of FIG. 1 in accordance with embodiments.

As shown in FIG. 2, the elevator rail, rope or belt health monitoring system 100 includes a first light source 120a and a first detector or light sensing device 130a. The first light source 120a and the first light sensing device 130a may be aligned with each other where alignment is defined as being perpendicular to the direction of relative motion between the side of the elevator car 23 and the scattering surface 60a. The elevator rail, rope or belt health monitoring system 100 may also include a second light source 120b and a detector or second light sensing device 130b which can also be aligned with each other. The second light source 120b and the second light sensing device 130b are located at a first distance D1 from the first light source 120a and the first light sensing device 130a.

The elevator rail, rope or belt health monitoring system 100 may include additional light sources and detectors or light sensing devices. Advantageously, additional light sources may be able to provide increased accuracy and/or redundancy, as will be discussed further below. For instance, FIG. 2 shows a third light source 120c and a third light sensing device 130c which are aligned with each other at a second distance D2 from the first light source 120a and the first light sensing device 130a.

The light sources 120a-120c may be provided as light emitting diodes (LEDs), including organic light emitting diodes (OLEDS), or lasers of one or multiple operational wavelengths. That is, the light sources 120a-120c may be provided as LEDs or lasers that emit visible light in various colors, LEDs or lasers that emit ultraviolet (UV) wavelength radiation or LEDs or lasers that emit infrared (IR) wavelength radiation. In some cases, the light sources 120a-120c may be provided as a laser diode that emits light at near telecom bandwidths (e.g., about 1-10 μm or ~1.5 μm). In accordance with further embodiments, the light sources 120a-120c may also include other light sources such as, for example, an incandescent light bulb, an arc lamp, a gas discharge lamp or any other light source of any wavelength. In any case, the light sources 120a-120c emit light or radiation 122a-122c onto the scattering surface 60a and may, in some cases, emit the light or radiation 122a-122c at selected impulse rates.

In accordance with embodiments, the selected impulse rates may be predefined as rates that are consistent with accuracy considerations (e.g., fractional second impulses) and/or power saving considerations (e.g., single impulses take over many days or weeks at a time).

The light sensing devices 130a-130c may be provided as one or more photodetectors or photodiodes (PDs) and may be designed to be sensitive to particular wavelengths. That is, the light sensing devices 130a-130c may be PDs that are sensitive to visible light of various colors, UV or IR radiation or light or radiation at near telecom bandwidths (e.g., about ~1.5 μm).

Figure 3:
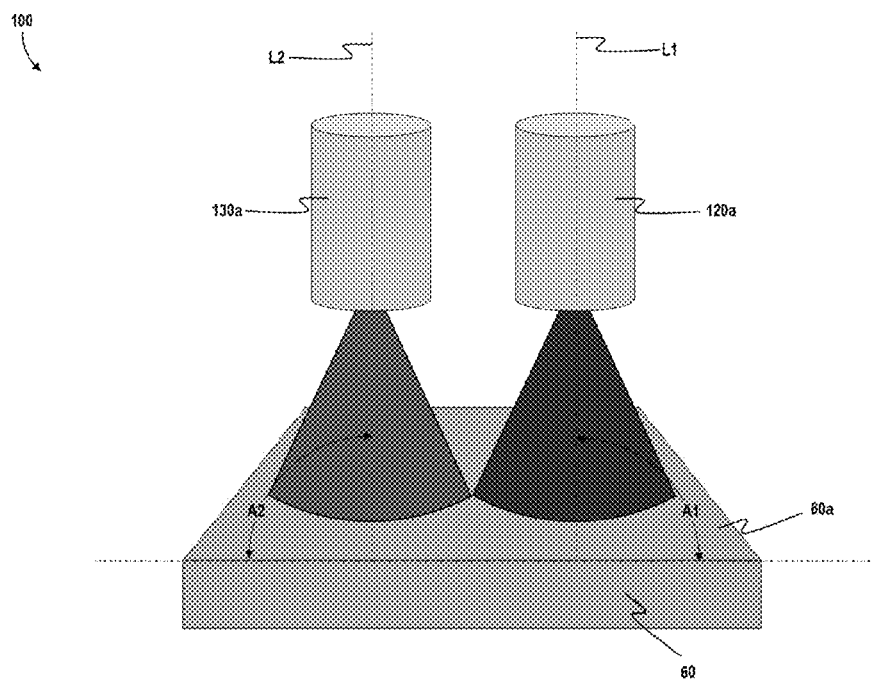
FIG. 3 illustrates a schematic view of relative orientations of a light source, a detector and a scattering surface within the elevator rail health monitoring system of FIG. 2 in accordance with embodiments.
Figure 4:
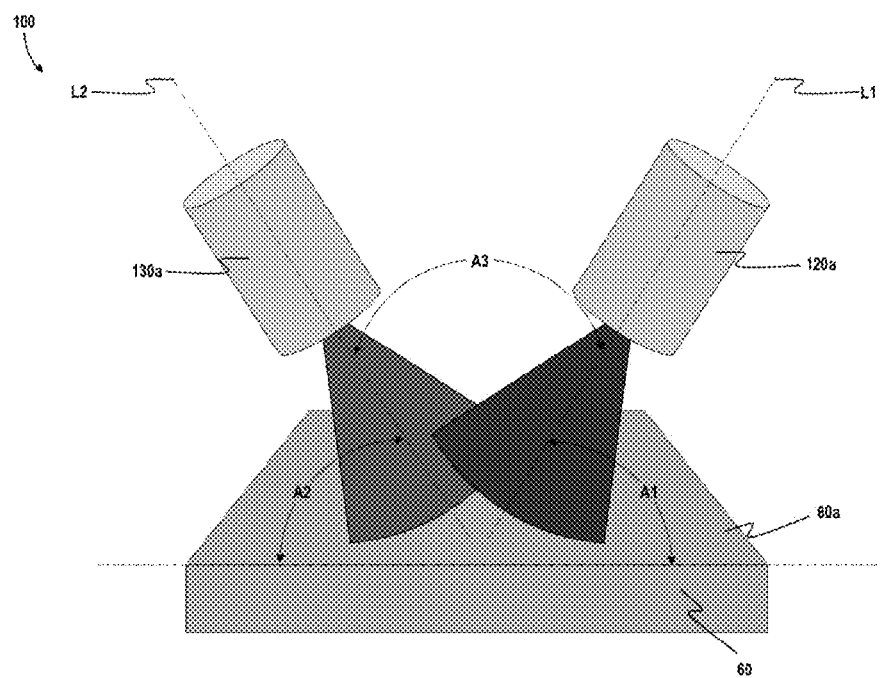
FIG. 4 illustrates a schematic view of relative orientations of an emitter, a detector and a scattering surface within the elevator rail health monitoring system of FIG. 2 in accordance with embodiments.

With reference to FIGS. 3 and 4, the light sources 120a-120c and the light sensing devices 130a-130c may be oriented at various angles relative to the scattering surface 60a to detect different types of scattered light or radiation. In the example of FIG. 3, the first light source 120a and the first light sensing device 130a are both oriented perpendicularly with respect to the scattering surface 60a. That is, a first angle A1 between the scattering surface 60 and a first axis L1 of the first light source 120a is equal to about 90 degrees and a second angle A2 between the scattering surface 60a and a second axis L2 of the first light sensing device 130a is equal to about 90 degrees. In the example of FIG. 4, the first light source 120a and the first light sensing device 130a are oriented non-perpendicularly with respect to the scattering surface 60a. That is, a first angle A1 between the scattering surface 60a and a first axis L1 of the first light source 120a is not equal to 90 degrees, a second angle A2 between the scattering surface 60 and a second axis L2 of the first light sensing device 130a is not equal to 90 degrees and a first angle of coincidence A3 between the first light source 120a and the first light sensing device 130a is non-zero and less than 180 degrees. The first angle of coincidence A3 may be defined as the angle between the first axis L1 and the second axis L2.

In accordance with embodiments, each set of light sources and light sensing devices can have their own angle of coincidence.

In the case of the light sources 120a-120c being LEDs that emit visible light at varying wavelengths or lasers and the light sensing devices 130a-130c being configured to detect such visible light or such laser light (e.g., as photodetectors or photodiodes), the light sensing devices 130a-130c may be configured to measure scattered light signals that are scattered off the scattering surface 60a in various directions especially where the angle of coincidence between light sources and sensing devices is non-zero and less than 180 degrees. In such cases, it is to be understood that light scatters differently when it is scattered off of areas of the scattering surface 60a that are of differing quality. That is, as the elevator rail, rope or belt health monitoring system 100 and the scattering surface 60a move relative to one another, each of the light sensing devices 130a-130c jointly or separately records the intensity of scattered light at multiple wavelengths/angles.

Figure 5A:
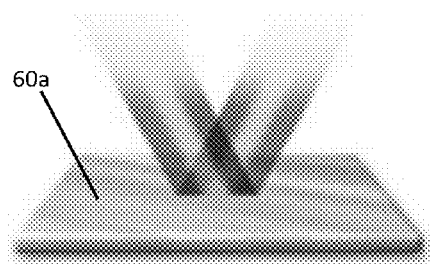
FIGS. 5A and 5B illustrate specular and diffuse scattering of light from surfaces of differing quality.
Figure 5B:
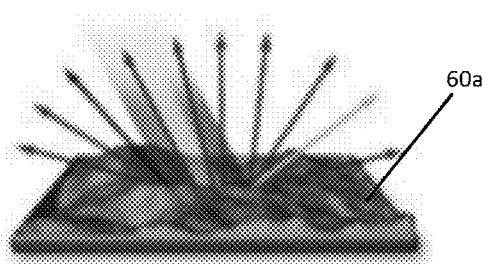

With reference to FIGS. 5A and 5B, the scattering patterns of light emitted from the light sources 120a-120c and scattered off of the scattering surface 60a will be related to, for example, a cleanliness of the scattering surface. For example, as shown in FIG. 5A, the scattering pattern is mostly specular when the scattering surface 60a is clean and thus a forward scattering signal will be relatively enhanced while the backscatter signal will be relatively reduced. On the one hand, as shown in FIG. 5B, the scattering pattern will be more diffuse when the scattering surface 60a is dirty, rusted or otherwise compromised. Thus, in this case, the backward scattered signal will be relatively enhanced while the forward scattered signal will be relatively reduced.

With the above in mind, it is seen that the elevator rail, rope or belt health monitoring system 100 will allow for a monitoring of the health of an elevator rail, rope or belt by way of a monitoring of the reflection properties thereof.

In the case of the light sources 120a-120c being UV, visible, or IR LEDs or diode lasers that are tuned to near telecom wavelengths (e.g., about ~1.5 μm) and the light sensing devices 130a-130c being sensitive to such radiation, the light sensing devices 130a-130c may be configured to measure a response of matter that is disposed on the scattering surface 60a. Such matter may be provided as waxes, oils, debris and/or lubricants that may be needed at certain quantities for proper operations or that may be detrimental to such proper operations. In any case, by tuning the light sources 120a-120c to emit light that causes a certain response by that matter and by tuning the light sensing devices 130a-130c to sense such responses, the elevator rail or rope health monitoring system 100 can identify which if any waxes, oils, debris and lubricants are present on the scattering surface 60a (and in what quantity) as the elevator rail, rope or belt health monitoring system 100 and the scattering surface 60a move relative to one another.

Figure 6A:
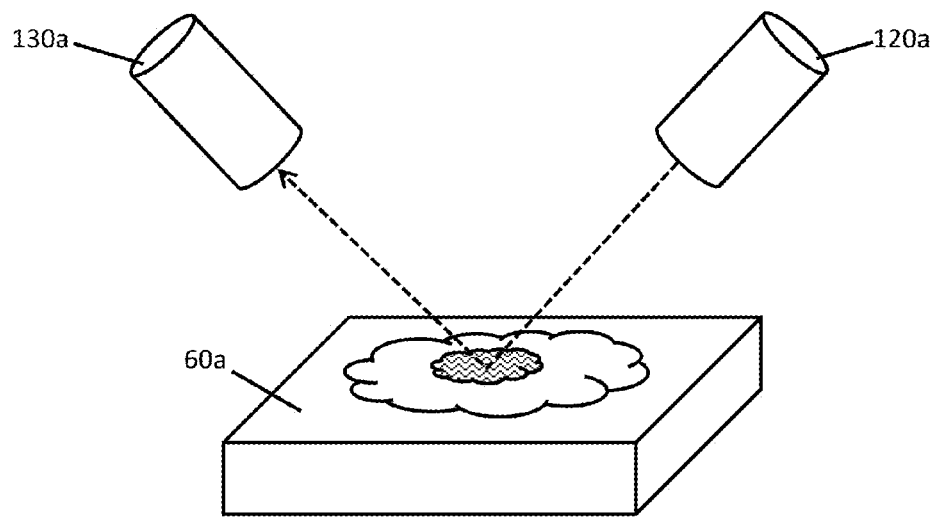
FIGS. 6A, 6B and 6C illustrate radiation emissions for detecting different waxes, oils or lubricants.
Figure 6B:
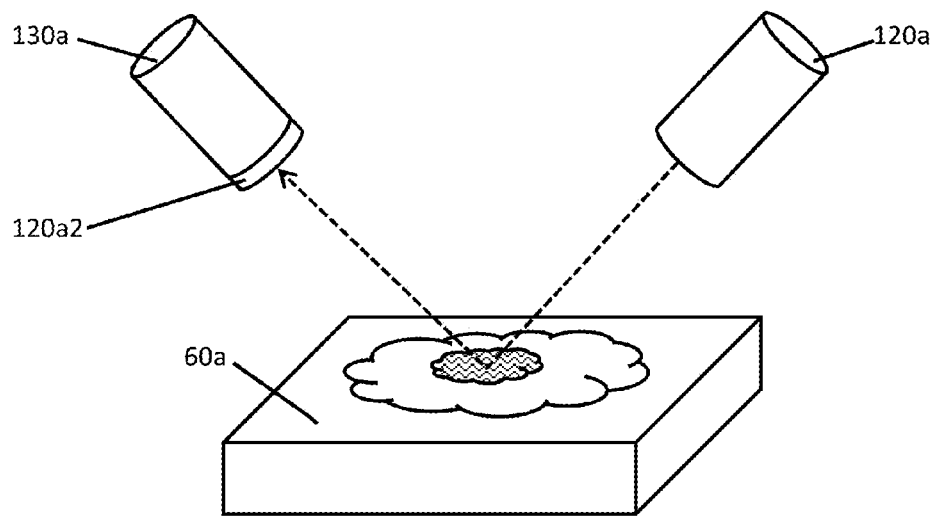
Figure 6C:
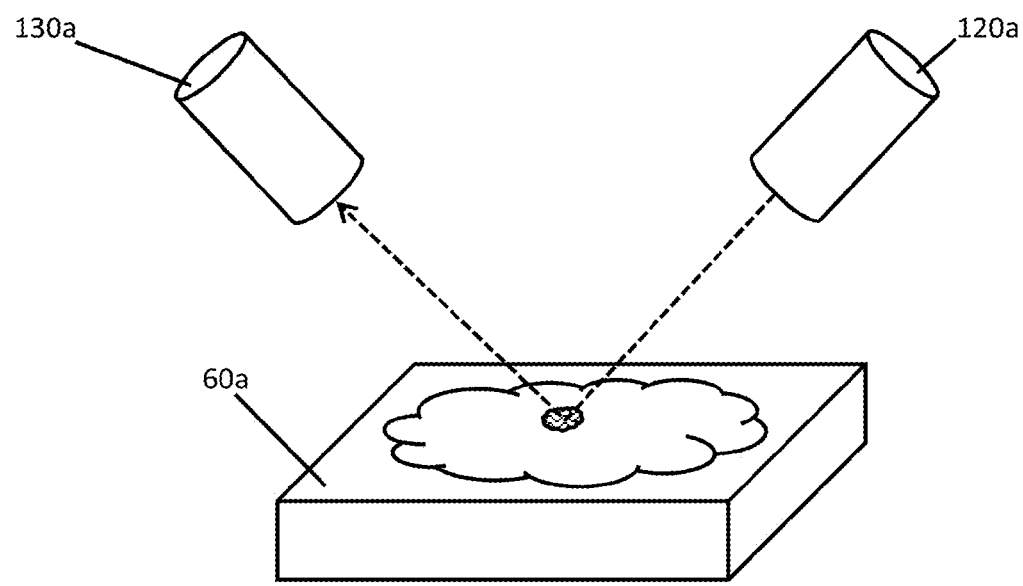

With reference to FIGS. 6A, 6B and 6C, exemplary operations of the elevator rail, rope or belt health monitoring system 100 are illustrated. As shown in FIG. 6A, in order to detect the presence and quantity of waxes, oils, debris and lubricants that absorb UV radiation, a light source 120a is provided as a UV LED or laser and a light sensing device 130a is provided as a photodetector or photodiode that is sensitive to waxes, oils, debris and lubricants that are highly absorptive of UV radiation. As shown in FIG. 6B, since some waxes, oils, debris and lubricants fluoresce, the light sensing device 130a of FIG. 6A may be further provided with an additional optical filtering element 130a2. As shown in FIG. 6C, the light source 120a is provided as a diode laser that can be tuned to near the telecom wavelengths (e.g., about 1-10 μm~1.5 μm, or other wavelengths of interest) where molecules of certain waxes, oils and lubricants can be probed (specifically, their respective CH bonds) with fairly high certainty.

With reference to FIG. 7, a method of monitoring elevator rail health is provided and is particularly useful for the embodiments illustrated in FIGS. 5A and 5B. The method includes moving a health monitor over scattering surface 60a (block 701), illuminating the scattering surface 60a with light emitted from a light source 120a-120c of the health monitor (block 702) and recording an intensity of scattered light scattered off the scattering surface 60a at a detector 130a-130c of the health monitor (block 703). The method further includes determining from the recorded intensity a ratio of forward scattered light to backward scattered light of the scattered light that is scattered off the scattering surface 60a (block 704). Finally, the method includes identifying that the scattering surface 60a exhibits a predefined (e.g., clean) condition in an event the determined ratio indicates an enhancement of the forward scattered light relative to the backward scattered light to a first predefined degree (block 705) and identifying that the scattering surface 60a exhibits a predefined (e.g., unclean, rusted, corroded, chipped, scratched, dented, burred, cracked or fractured) condition in an event the determined ratio indicates an enhancement of the backward scattered light relative to the forward scattered light to a second predefined degree (block 706). In some cases, the method may also include scheduling and executing a cleaning, maintenance, repair or replacement of the scattering surface 60a in accordance with a result of the identifying (block 707). That is, if the scattering surface 60a is found to be unclean, rusted, corroded, chipped, scratched, dented, burred, cracked or fractured, the method provided herein can be used to schedule a cleaning, maintenance, repair or replacement to return the scattering surface 60a to its original condition.

In accordance with embodiments, the method may include accounting for the presence of ambient light in the recording and determining and may be repeatable with respect to the scattering surface 60a and thus may include measuring conditional changes of the scattering surface 60a over time. Examples of this repetition and the measurement of conditional changes of the scattering surface 60a over time will be provided below.

For a given elevator rail, rope or belt health monitoring system 100, an initial run may be executed where the scattering surface 60a is a guide rail and is known to be sufficiently clean and without, rust, corrosion, chips, scratches, dents, burs, cracks or fractures. The ratio of forward scattered light to backward scattered light determined from this initial run can be used as a baseline against which later runs can be compared. At a later time, a subsequent run may be executed and may indicate that the ratio exhibits an enhancement of the backward scattered light. If this enhancement exceeds a predefined degree, which may be related as a percentage to the initial ratio of forward scattered light to backward scattered light (e.g., an enhancement percentage of 105% or more), the guide rail would be identified as being in an unclean (or rusted, corroded, chipped, scratched, dented, burred, cracked or fractured) condition at least at the location of the scattering surface 60a such that maintenance and repair are scheduled and conducted with respect to at least the scattering surface 60a.

As an additional matter, the scattering effect caused by the scattering surface 60a being unclean, rusted, corroded, chipped, scratched, dented, burred or cracked may be relatively consistent from one instance to another whereby the enhancement of the backward scattered light (or the forward scattered light, as the case may be) or a pattern of the enhancement can be used to determine exactly what type of situation is present at the scattering surface 60a. For example, if it is known that rust tends to enhance backward scattering more than a lack of cleanliness and the ratio derived from the subsequent run(s) exhibits a substantial enhancement of the backward scattered light that is more consistent with rust than with a lack of cleanliness, it may be understood that the scattering surface 60a is most likely rusted. In such a case, action can be taken to repair the scattering surface 60a of the rusted condition without the need to initially examine the region before taking action to determine whether the issue is one of cleanliness or rust. By contrast, if it is known that cracking or fracturing of the scattering surface 60a tends to enhance forward scattering and the ratio derived from the subsequent run(s) exhibits a substantial enhancement of the forward scattered light (when one would expect at least a certain degree of enhancement to backward scattered light), it may be understood that the scattering surface 60a is most likely cracked or fractured. In such a case, immediate action can be taken to repair or replace the scattering surface 60a without the need to initially examine the region before taking action.

With reference to FIG. 8, a method of monitoring elevator rail health is provided and is particularly useful for the embodiments illustrated in FIGS. 6A, 6B and 6C. The method includes moving a health monitor over the scattering surface 60a (block 801), irradiating the scattering surface 60a with radiation emitted from an emitter of the health monitor (i.e., any one or more of the light sources 120a-120c) at a wavelength selected for detecting wax, oil, debris or lubricant on the scattering surface 60a (block 802) and detecting a response of the wax, oil, debris or lubricant on the scattering surface to the radiation at a detector 130a-130c of the health monitor (block 803). The method further includes determining from the detected response an amount of the wax, oil, debris or lubricant on the scattering surface 60a (block 804). Finally, the method includes identifying that the scattering surface 60a exhibits a predefined (e.g., overly clean and unlubricated) condition in an event the determined amount is less than the predefined threshold (block 805) and identifying that the scattering surface 60a exhibits a predefined (e.g., unclean and appropriately lubricated) condition in an event the determined amount exceeds the predefined threshold (block 806). In some cases, the method may also include scheduling and executing maintenance of the scattering surface in accordance with a result of the identifying (block 807). That is, if the scattering surface 60a is found to be overly clean and un- or insufficiently lubricated, the method can be used to schedule maintenance to return the scattering surface 60a to its original lubricated condition.

In accordance with embodiments, the method may include accounting for the presence of ambient light in the detecting and identifying and may be repeatable with respect to the scattering surface 60a and thus may include measuring conditional changes of the scattering surface 60a over time. Examples of this repetition and the measurement of conditional changes of the scattering surface 60a over time will be provided below.

For a given elevator rail, rope or belt health monitoring system 100, an initial run may be executed where the scattering surface 60a is a guide rail and is known to be sufficiently lubricated. The response of this lubrication to the emitted radiation can be used as a baseline against which later runs can be compared. At a later time, a subsequent run may be executed and may indicate from a reduced response to a similar exposure that the amount of lubricant is diminished as compared to the baseline. If the degree of this diminishment exceeds a predefined threshold, the guide rail would be identified as being in a clean or un- or insufficiently lubricated condition such that maintenance and repair are scheduled and conducted top return the scattering surface 60a to its original lubricated condition.

While the disclosure is provided in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that the exemplary embodiment(s) may include only some of the described exemplary aspects. Accordingly, the disclosure is not to be seen as limited by the foregoing description, but is only limited by the scope of the appended claims.

What is claimed is:

1. A method of monitoring component health, the method comprising:
    disposing a health monitor on an elevator which is movable relative to a structure in which a component is fixed:
    moving the elevator relative to the structure and the component such that the health monitor is moved over a scattering surface of the component;
    emitting light of various wavelengths toward the scattering surface from a light source of the health monitor;
    observing one or more responses of the scattering surface to the light of the various wavelengths at a detector of the health monitor; and
    identifying a condition of the scattering surface from the observed one or more responses of the scattering surface to the light of the various wavelengths.

2. The method according to claim 1, wherein the light source comprises one or more light sources and the detector comprises one or more photodetectors.

3. The method according to claim 1, wherein:
    the emitting comprises illuminating the scattering surface at an angle from the light source;
    the observing comprises recording an intensity of scattered light scattered off the scattering surface at the detector; and
    the identifying of the condition comprises:
    determining from the recorded intensity a ratio of forward scattered light to backward scattered light of the scattered light that is scattered off the scattering surface; and
    identifying that the scattering surface exhibits one or more of an unclean, a rusted, a corroded, a chipped, a scratched, a dented, a burred, a cracked or a fractured condition in an event the determined ratio indicates an enhancement of the backward scattered light relative to the forward scattered light to a predefined degree.

4. The method according to claim 1, wherein:
the emitting comprises irradiating the scattering surface with radiation from the light source at a wavelength selected for detecting wax, oil, debris or lubricant on the scattering surface;
the observing comprises detecting a response of the wax, oil, debris or lubricant on the scattering surface to the radiation at the detector; and
the identifying comprises:
determining from the detected response an amount of the wax, oil, debris or lubricant on the scattering surface; and
identifying that the scattering surface exhibits an unclean and appropriately lubricated condition in an event the determined amount exceeds a predefined threshold.

5. The method according to claim 1, wherein the method is repeatable with respect to the scattering surface and comprises:
measuring conditional changes of the scattering surface over time; and
scheduling and executing a cleaning, maintenance, repair or lubrication of the scattering surface in accordance with a result of the identifying.

6. The method according to claim 1, further comprising accounting for ambient light in the observing and identifying.

7. A method of monitoring elevator rail, rope or belt health, comprising:
disposing a health monitor on an elevator which is movable relative to a structure in which a component is disposed;
moving the elevator relative to the structure such that the health monitor moves over a scattering surface of the component;
illuminating the scattering surface with light emitted from a light source of the health monitor;
recording an intensity of scattered light scattered off the scattering surface and received by a detector of the health monitor;
determining, from the recorded intensity of scattered light, a ratio of forward scattered light to backward scattered light of the scattered light that is received by the detector; and
identifying that the scattering surface exhibits a predefined condition in an event the determined ratio indicates an enhancement of the backward scattered light relative to the forward scattered light to a predefined degree.

8. The method according to claim 7, wherein the illuminating comprises illuminating the scattering surface at an angle.

9. The method according to claim 7, wherein the light source comprises one or more light sources.

10. The method according to claim 7, wherein the detector comprises one or more photodetectors.

11. The method according to claim 7, wherein the identifying comprises:
identifying that the scattering surface exhibits one or more of a clean, a non-rusted, a non-corroded, a non-chipped, a non-scratched, an undented, an un-burred, a non-cracked and a non-fractured condition in an event the determined ratio indicates an enhancement of the forward scattered light relative to the backward scattered light to a first predefined degree; and
identifying that the scattering surface exhibits one or more of an unclean, a rusted, a corroded, a chipped, a scratched, a dented, a burred, a cracked or a fractured condition in an event the determined ratio indicates an enhancement of the backward scattered light relative to the forward scattered light to a second predefined degree.

12. The method according to claim 7, wherein the method is repeatable with respect to the scattering surface and comprises measuring conditional changes of the scattering surface over time.

13. The method according to claim 7, further comprising scheduling and executing a cleaning, maintenance or repair of the scattering surface in accordance with a result of the identifying.

14. A method of monitoring elevator rail, rope or belt health, comprising:
disposing a health monitor on an elevator which is movable relative to a structure in which a component is disposed;
moving the elevator relative to the structure such that the health monitor moves over a scattering surface of the component;
irradiating the scattering surface with radiation emitted from an emitter of the health monitor at a wavelength selected for detecting wax, oil, debris or lubricant on the scattering surface;
detecting a response of the wax, oil, debris or lubricant on the scattering surface to the radiation at a detector of the health monitor;
determining from the detected response an amount of the wax, oil, debris or lubricant on the scattering surface; and
identifying that the scattering surface exhibits a predefined condition in an event the determined amount exceeds a predefined threshold.

15. The method according to claim 14, wherein the irradiating comprises irradiating the scattering surface at an angle.

16. The method according to claim 14, wherein the light source comprises an ultraviolet (UV) light emitting diode (LED), an organic light emitting diode (OLED) or a UV laser and the detector comprises an ultraviolet (UV) sensitive photodetector.

17. The method according to claim 14, wherein the light source comprises a light emitting diode (LED), an organic light emitting diode (OLED) or a laser that is tuned to visible or infrared (IR) wavelengths and the detector comprises a complementary wavelength sensitive photodetector.

18. The method according to claim 14, wherein the identifying comprises:
identifying that the scattering surface exhibits a clean and an unlubricated condition in an event the determined amount is less than the predefined threshold; and
identifying that the scattering surface exhibits an unclean and appropriately lubricated condition in an event the determined amount exceeds the predefined threshold.

19. The method according to claim 14, wherein the method is repeatable with respect to the scattering surface and comprises measuring conditional changes of the scattering surface over time.

20. The method according to claim 14, further comprising scheduling and executing a lubrication of the scattering surface in accordance with a result of the identifying.

* * * * *